(12) United States Patent
Murata et al.

(10) Patent No.: US 8,696,993 B2
(45) Date of Patent: Apr. 15, 2014

(54) METHOD OF RAISING TEMPERATURE OF RECEIVED OBJECT, AND ANALYZING DEVICE

(75) Inventors: Yasuhito Murata, Kyoto (JP); Junichi Oka, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 1450 days.

(21) Appl. No.: 10/584,219

(22) PCT Filed: Dec. 24, 2004

(86) PCT No.: PCT/JP2004/019380
§ 371 (c)(1),
(2), (4) Date: Jun. 23, 2006

(87) PCT Pub. No.: WO2005/064348
PCT Pub. Date: Jul. 14, 2005

(65) Prior Publication Data
US 2007/0148780 A1    Jun. 28, 2007

(30) Foreign Application Priority Data
Dec. 25, 2003 (JP) .................................. 2003-429040

(51) Int. Cl.
*G05D 23/00* (2006.01)
*G05D 23/30* (2006.01)
*G05D 23/32* (2006.01)

(52) U.S. Cl.
USPC ................ 422/109; 237/2 A; 237/12; 702/99; 702/130; 236/1 C; 250/429; 436/147

(58) Field of Classification Search
USPC ..................... 436/147; 422/51, 102; 250/429; 137/334–341; 236/20; 237/2 R, 2 A
See application file for complete search history.

(56) References Cited

U.S. PATENT DOCUMENTS

| 4,679,615 A | 7/1987 | Livne |
| 5,410,130 A | 4/1995 | Braunstein |
| 5,475,610 A * | 12/1995 | Atwood et al. ............... 700/269 |
| 5,720,406 A | 2/1998 | Fassbind et al. |

FOREIGN PATENT DOCUMENTS

| JP | 6-14968 | 2/1994 |
| JP | 7-167865 | 7/1995 |
| JP | 9-189703 | 7/1997 |
| JP | 9-304269 | 11/1997 |
| JP | 11-83802 | 3/1999 |
| JP | 2001-318101 | 11/2001 |
| WO | WO 96/23249 | 8/1996 |

* cited by examiner

*Primary Examiner* — Paul Hyun
*Assistant Examiner* — Robert Eom
(74) *Attorney, Agent, or Firm* — Fox Rothschild LLP

(57) ABSTRACT

The present invention relates to an analyzing apparatus (1) for analyzing a sample using a container (2) accommodating reagents sealed therein, while raising the temperature of the reagents up to a predetermined temperature. The analyzing apparatus (1) comprises a first temperature measuring means (31) for measuring temperature of the container (2), a second temperature measuring means (32) for measuring temperature around the container (2), a heater (4) for supplying heat energy to the container (2), and a controller for controlling the heater (4) based on a measurement result at the first and second measuring means (31, 32).

11 Claims, 5 Drawing Sheets

METHOD OF RAISING TEMPERATURE OF RECEIVED OBJECT, AND ANALYZING DEVICE

TECHNICAL FIELD

The present invention relates to a technique for raising the temperature of an object contained in a container to a predetermined temperature. Specifically, the present invention relates to a technique for controlling the temperature of liquid contained in a cartridge used in an analyzing apparatus for sample analysis.

BACKGROUND ART

In sample analysis after reaction between the sample and reagents in an analyzing apparatus, temperature of the sample and the reagents or temperature of reaction liquid of the sample and the reagents is raised up to a predetermined reaction temperature for ensuring uniform reaction temperature. In temperature raising of the reagents, for example, a container accommodating the reagents is brought in contact with a heat medium (using e.g. water, air, or a metal block) capable of temperature control. (See the following patent documents 1, 2.)

In use of the analyzing apparatus, the reagents may be taken out of e.g. bottles in which the reagents are stored, and then dispensed into a container for analysis, or the reagents may be accommodated in a cartridge in advance. (See the following patent document 3.) In the cartridge, the reagents are sealed for preventing evaporation, and for convenience of transfer.

When the reagents are sealed in the container, it is unfavorable to measure the temperature of the reagents directly. Specifically, for the temperature measurement, the analyzing apparatus requires a mechanism for exposing the reagents to the air, which makes the structure of the analyzing apparatus complicated, thereby increasing the product cost. Further, if the reagents are exposed to the air during the temperature raising, the reagents may evaporate. When immune reaction is utilized for the sample analysis, an antibody is accommodated in the cartridge as a reagent. As an antibody is generally expensive as a reagent, its amount in the cartridge is reduced as much as possible. Thus, when using an antibody as a reagent, the evaporation of the antibody, even at very small amount, may affect the result of the sample analysis. The amount of the antibody in the cartridge may be increased in consideration of the amount of evaporation, however, as described above, the antibody is expensive to use as a reagent, thereby increasing the cost.

For example, a predetermined amount of heat energy may be constantly supplied to the container for raising the temperature of the reagents, without measuring the temperature of the reagents directly. However, as the temperature raising of the reagents is affected by ambient temperature around the container, if the ambient temperature varies by analysis, the reaction temperature varies by analysis, thereby lowering the accuracy of analysis.

DISCLOSURE OF THE INVENTION

An object of the present invention is to properly raise temperature of a contained object sealed in a container up to a target temperature, without being affected by ambient temperature, so that reaction temperature of sample and the reagent is uniform, thereby improving accuracy of analysis.

According to a first aspect of the present invention, there is provided a method of raising temperature of a contained object sealed in a container, up to a predetermined temperature. The method comprises a first step for measuring temperature of the container and ambient temperature around the container, a second step for determining an amount of heat energy necessary for raising the temperature of the contained object up to the predetermined temperature, based on the container temperature and the ambient temperature, and a third step for supplying heat energy to the container, based on a result of the second step.

The container comprises a receptacle having an opening and a seal for sealing the opening. The seal is measured to obtain the container temperature in the first step.

The method of raising temperature of contained object according to the present invention further comprises a fourth step, performed between the first step and the second step, for estimating temperature of the contained object based on the container temperature and the ambient temperature. Here, in the second step, the estimated temperature is checked to be higher or lower than an additional predetermined temperature set lower than said predetermined temperature, so that the amount of heat energy to be supplied to the container is determined based on the check result. Specifically, in the second step, the amount of heat energy to be supplied to the container is determined so that the amount of heat energy to be supplied to the container per unit time is smaller when the estimated temperature becomes higher than the additional predetermined temperature, than when the estimated temperature is lower than the additional predetermined temperature.

In the fourth step, the estimated temperature is calculated based on a correlation, examined in advance, of difference between the temperatures of the contained object and the container measured when a predetermined time passes after the beginning of temperature raising, with the ambient temperature measured when a predetermined time passes after the beginning of temperature raising. Preferably, the predetermined time is set within initial stage of raising the temperature of the contained object up to the predetermined temperature where the temperature rising amount of the contained object and the container per unit time is relatively large. The predetermined time is set at a value selected from a range of, for example, 10 seconds to 2 minutes, preferably of 30 seconds to 1 minute, after the beginning of temperature raising.

In the third step, the container is brought into contact with a heat medium, and control of the amount of heat energy to be supplied to the container is performed by controlling the temperature of the heat medium.

According to a second aspect of the present invention, there is provided a method of raising temperature of contained object sealed in a container, up to a predetermined temperature, by supplying heat energy to the container brought into contact with a heating block. The method comprises a first step for measuring ambient temperature around the container immediately before raising temperature, a second step for determining an amount of heat energy necessary for raising the temperature of the contained object up to a predetermined temperature, in consideration of the ambient temperature, and a third step for supplying heat energy to the container via the heating block, based on a result of the second step.

In the second step, the amount of heat energy to be supplied to the container is determined by setting temperature of the heating block as well as time for which the temperature of the heating block is to be maintained. Specifically, in the second step, supplying time of the heat energy is divided into a first period from beginning of the supply of the heat energy until a predetermined time passes, and a second period from after the predetermined time passes until the supply of the heat energy ends. The amount of heat energy to be supplied to the container is determined so that the amount of heat energy to be supplied per unit time is smaller in the second period than in the first period.

In the second step, the amount of heat energy necessary for raising the temperature of the contained object up to the predetermined temperature is calculated based on a correlation examined in advance. The correlation is the difference between the temperatures of the contained object and the container measured when a predetermined time passes after the beginning of temperature raising, with the ambient temperature measured when a predetermined time passes after the beginning of temperature raising. The predetermined time is set within initial stage of raising the temperature of the contained object up to the predetermined temperature where the temperature rising amount of the contained object and the container per unit time is relatively large. The predetermined time is set at a value selected from a range of, for example, 10 seconds to 2 minutes, preferably 30 seconds to 1 minute, after the beginning of temperature raising.

According to a third aspect of the present invention, there is provided an analyzing apparatus for analyzing a sample using a container accommodating reagents sealed therein, while raising the temperature of the reagents up to a predetermined temperature. The analyzing apparatus comprises a first temperature measuring means for measuring temperature of the container, a second temperature measuring means for measuring temperature around the container, a heater for supplying heat energy to the container, and a controller for controlling the heater based on a measurement result at the first and second measuring means.

The container comprises a receptacle having an opening and a seal for sealing the opening. The first measuring means measures the seal to obtain the container temperature.

The heater comprises a heat medium (e.g. heating block) brought into contact with the container for supplying heat energy to the container.

The analyzing apparatus according to the present invention further comprises a calculator for estimating temperature of the reagents, based on measurement result at the first and the second temperature measuring means. In this case, the calculator estimates the temperature of the reagents based on a correlation, examined in advance, of the difference between the temperatures of the contained object and the container measured when a predetermined time passes after the beginning of temperature raising, with the ambient temperature measured when a predetermined time passes after the beginning of temperature raising.

Preferably, the controller checks if the estimated temperature is higher or lower than an additional predetermined temperature set lower than said predetermined temperature, and controls the heater so that the amount of heat energy to be supplied to the container per unit time is smaller when the estimated temperature becomes higher than the additional predetermined temperature, than when the estimated temperature is lower than the additional predetermined temperature.

According to a fourth aspect of the present invention, there is provided an analyzing apparatus for analyzing a sample using a container accommodating reagents sealed therein, while raising the temperature of the reagents up to a predetermined temperature. The analyzing apparatus comprises a heating block brought into contact with the container for supplying heat energy to the container, a temperature measuring means for measuring ambient temperature around the container, a calculator for calculating an amount of heat energy necessary for raising temperature of the reagents up to a predetermined temperature, based on a result measured by the temperature measuring means immediately before raising temperature, and a controller for controlling the heating block based on a calculation result at the calculator.

For example, the calculator calculates the amount of heat energy necessary for raising temperature of the container up to the predetermined temperature, based on an equation formed in consideration of a correlation examined in advance and on the ambient temperature. The correlation is difference between the temperatures of the contained object and the container measured when a predetermined time passes after the beginning of temperature raising, with the ambient temperature measured when a predetermined time passes after the beginning of temperature raising. The predetermined time is set within initial stage of raising the temperature of the contained object up to the predetermined temperature where the temperature rising amount of the contained object and the container per unit time is relatively large.

Here, in the third and fourth aspects of the present invention, "reagents" include not only reagents reacting with a sample, but also diluent, cleaning liquid, and catalyst. Further, in the third and fourth aspects of the present invention, "predetermined time" is set at a value selected from a range of, for example, 10 seconds to 2 minutes, preferably 30 seconds to 1 minute, after the beginning of temperature raising.

BEST MODE FOR CARRYING OUT THE INVENTION

Figure 1:
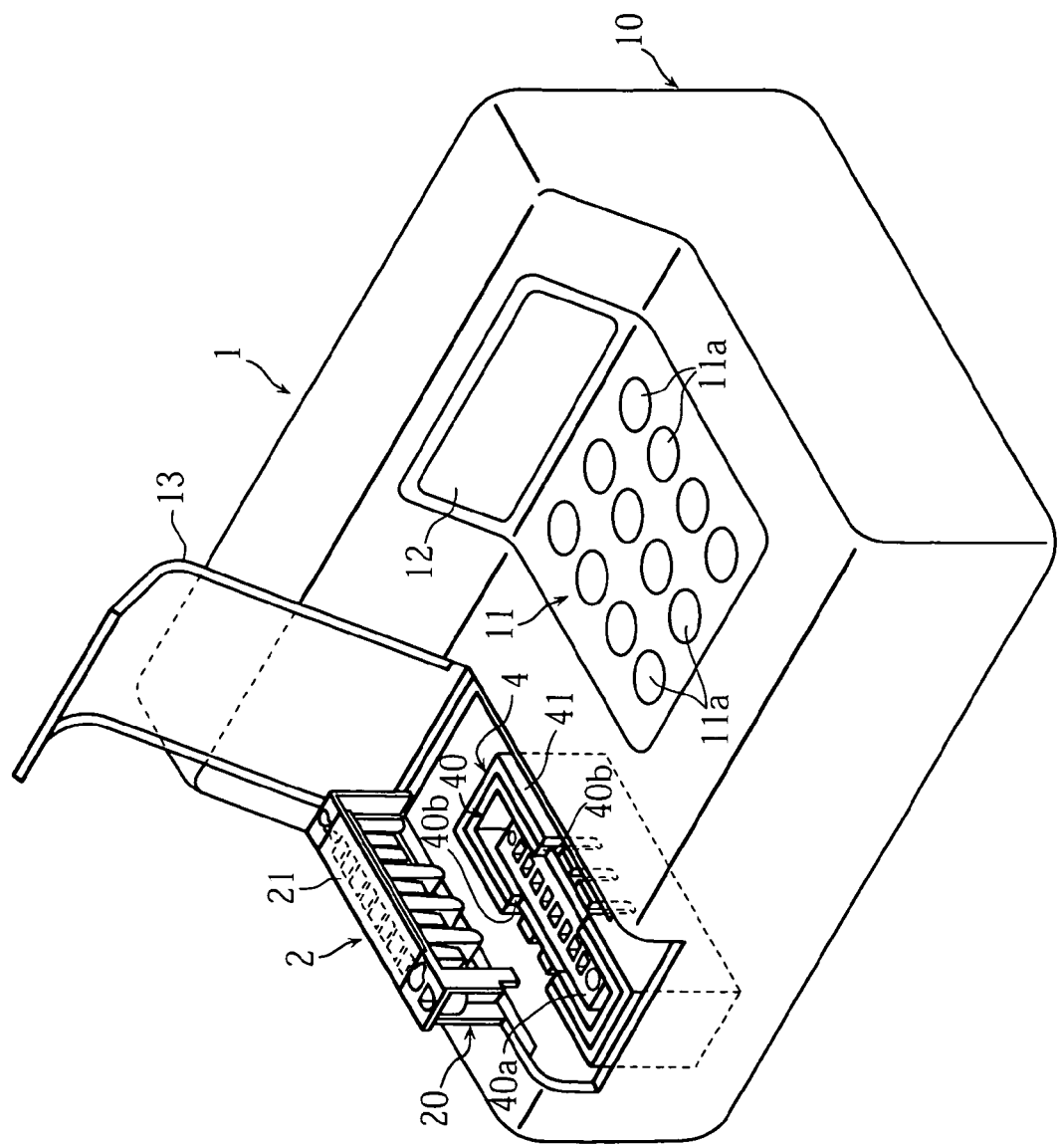
FIG. 1 is an overall perspective view illustrating an example of an analyzing apparatus according to the present invention.
Figure 2:
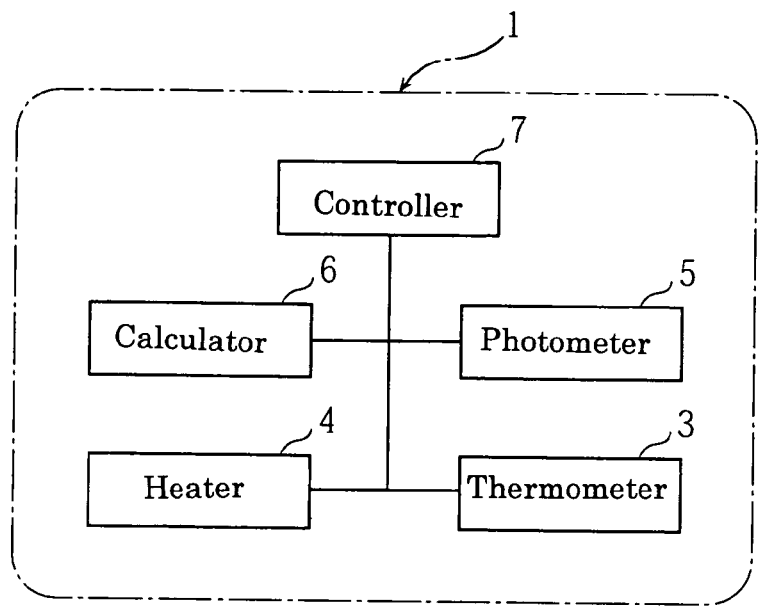
FIG. 2 is a block diagram of the analyzing apparatus of FIG. 1.

As shown in FIG. 1, an analyzing apparatus 1 according to the present invention performs sample analysis using a cartridge 2 hermetically containing reagents, with a function of raising the temperature of the reagents. The analyzing apparatus 1 includes a housing 10 incorporating a thermometer 3, a heater 4, a photometer 5, a calculator 6, and a controller 7, as shown in FIG. 2.

Figure 3:
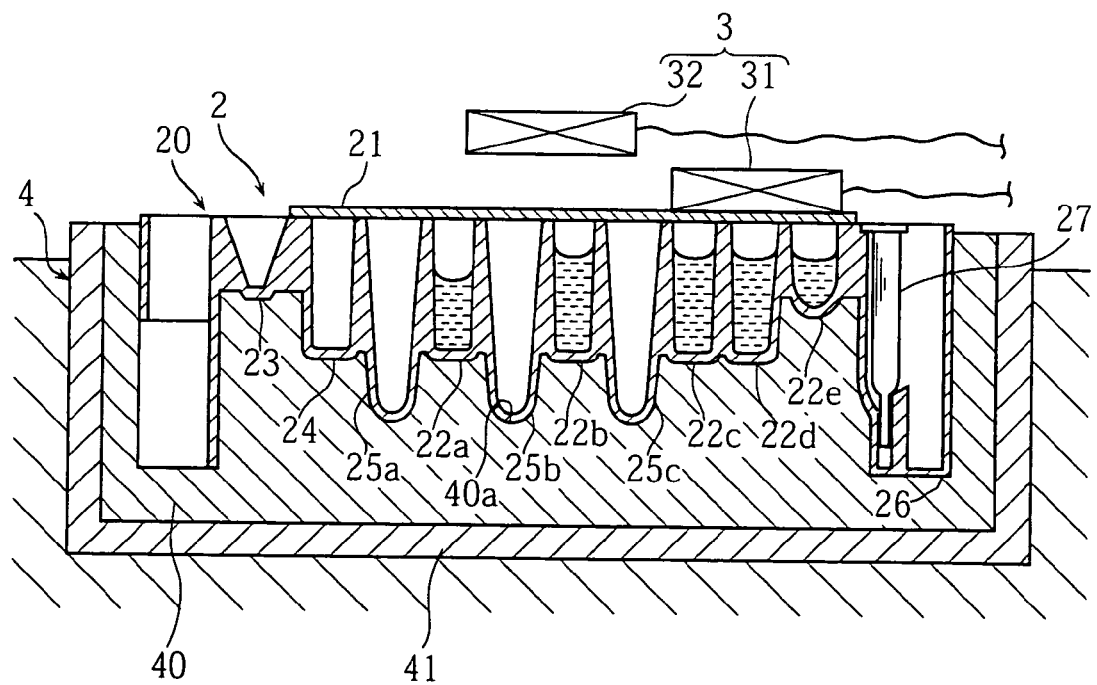
FIG. 3 is a sectional view illustrating a principal portion of the analyzing apparatus with a cartridge attached to a heater.

As shown in FIGS. 1 and 3, the cartridge 2 includes a body 20 and a seal 21. As shown in FIG. 3, the body 20 includes a plurality of storage wells 22a-22e, a sample well 23, a preparation well 24, a plurality of reaction wells 25a-25c, and a disposal well 26. Each of the storage wells 22a-22e contains a reagent such as an antibody for reaction with a sample (analyte), a diluent, a cleaning liquid, or an inert liquid, for example. The sample well 23 contains a sample. In the sample well 23, a user directly supplies a sample, or the analyzing apparatus automatically supplies a sample that the user put into the analyzing apparatus 1 in advance. In the preparation well 24, a mixture liquid is prepared for reaction with the sample. In the reaction wells 25a-25c, the sample reacts with the mixture liquid to produce reaction liquid, and the reaction liquid is optically detected. In the disposal well 26, a cleaning liquid used for cleaning a pipette tip 27 is disposed. The body 20 is integrally molded of a transparent resin material, for example. The seal 21 collectively seals openings of the wells 22a-22e, 24, 25a-25c, except the sample well 23 and the disposal well 26. The seal 21 is made of e.g. a metal material such as aluminum, which can be easily broken by e.g. the pipette tip 27 and has heat conductivity higher than the body 20.

As shown in FIG. 1, the housing 10 is provided with an operation panel 11, a display panel 12, and a cover 13. The operation panel 11 includes a plurality of switches 11a. In the analyzing apparatus 1, the user operates the switches 11a to generate signals for performing various actions (analyzing or printing), or to perform various settings (setting analytical condition, inputting an examinee's ID, and so on). The display panel 12 displays a result of analysis or an error message, and also displays an operating procedure or a current state in setting. The cover 13 selects between the state in which the heater 4 is exposed and the cartridge 2 can be taken in or out, and the state in which the inside of the housing 10 is shielded from light.

As shown in FIG. 3, the thermometer 3 includes a first and a second temperature measuring members 31, 32. The first temperature measuring member 31 measures the temperature of the cartridge 2. When the cartridge 2 is incorporated in the housing 10 and the cover 13 (see FIG. 1) is closed, the first temperature measuring member 31 comes into contact with the seal 21 of the cartridge 2. The first temperature measuring member 31 is, for example, provided on the rear side of the cover 13 and comes into contact with the seal 21 when the cover 13 is closed, or provided at a position to move according to the closing movement of the cover 13 and comes into contact with the seal 21. The second temperature measuring member 32 measures the temperature around the cartridge 2 in the housing 10 (see FIG. 1). Examples of the first and the second temperature measuring members 31, 32 include a thermistor and a thermocouple, and the first and the second temperature measuring members 31, 32 are positioned so that they do not prevent the movement of a pipette (not shown) when preparing reaction liquid at the cartridge 2. The second temperature measuring member 32 may also be a non-contact thermometer such as a thermopile.

The heater 4 for supplying heat energy to the cartridge 2 includes a heating block 40 and an insulating holder 41.

Figure 4:
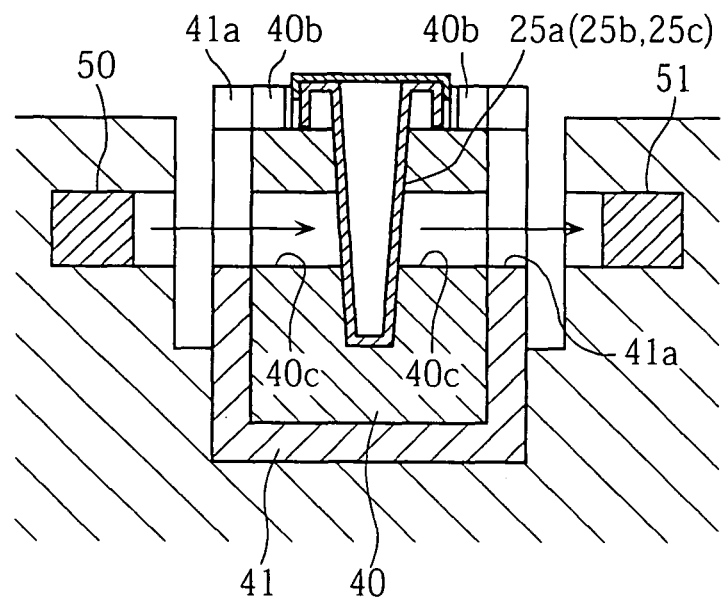
FIG. 4 is a sectional view illustrating a principal portion of the analyzing apparatus with a cartridge attached to a heater.

As shown in FIGS. 1, 3, and 4, the heating block 4 is formed with a recess 40a, cutouts 40b, and a through-hole 40c. The recess 40a for holding the cartridge 2 has an inner shape corresponding to the external shape of the body 20 of the cartridge 2. Thus, when the heating block 40 holds the cartridge 2, the inner surfaces of the recess 40a contact the surfaces of the wells 22a-22e, 23, 24, and 25a-25c. The cutout 40b facilitates insertion and removal of the cartridge 2 relative to the heating block 40. The through-hole 40c allows light, emitted from a light source 50 of the photometer 5 as described below, to enter into the reaction wells 25a-25c, or allows the light, transmitting through the reaction wells 25a-25c, to travel toward a light receiving portion 51 of the photometer 5 as described below. The heating block 4 is made of e.g. a metal material having high heat conductivity such as copper or aluminum, and receives heat energy from a non-illustrated heat source or a heat source incorporated in the heating block.

The insulating holder 41 surrounds the heating block 40 for regulating thermal diffusion from the heating block 40, as shown in FIGS. 3 and 4. The insulating holder 4 is formed with a recess 41a corresponding to the form and function of the cutouts 40b and the through-hole 40c of the heating block 40. The insulating holder 41 is made of a material having heat conductivity lower than the heating block.

The photometer 5 shown in FIG. 2 includes a light source 50 and a light receiving portion 51, as shown in FIG. 4. The light source 50 emits light to the reaction wells 25a-25c. The light receiving portion 51 receives the light transmitting through the reaction wells 25a-25c. The light source 50 is a mercury lamp or a white LED, for example. In using such light source, though not shown, light from the light source 50 enters into a filter to select a light ray of a desired wavelength, and then the light ray is emitted to the reaction wells 25a-25c. The light receiving portion 51 is a photodiode, for example. In this case, the amount of light transmitting through the reaction wells 25a-25c is outputted as an electrical signal. In the photometer 5, the light receiving portion may also receive reflected light such as scattered light from the light source.

The calculator 6 shown in FIG. 2 performs various calculation. Specifically, the calculator 6 estimates the temperature of the reagents contained in the cartridge 2 (see FIG. 3), or calculates the concentration of a specific component in the sample. The estimation of the temperature of the reagents is performed based on measurement results at the first and the second temperature measuring members 31, 32 (see FIG. 3). The calculation of the concentration is performed based on a result of light receiving at the light receiving portion 51 (see FIG. 4).

The controller 7 controls the amount of heat to be supplied to the heating block 40, or the temperature of the heating block 40. While the analyzing apparatus 1 is switched on, if the cartridge 2 is not incorporated in the heating block 4, the controller 7 controls to keep the temperature of the heating block 40 at a reaction temperature, and if the cartridge 2 is incorporated in the heating block 40, the controller controls to raise the temperature of the reagents in the cartridge 2 to be a target temperature. This temperature control at the heating block 40 for raising the temperature of the reagents to be the target temperature is performed based on the temperature of the reagents estimated by the calculator 6. The controller 7 also controls the operation of the photometer 5 and the calculator 6.

The calculator 6 and the controller 7 may be made of CPU, ROM, and RAM.

On performing sample analysis by the analyzing apparatus 1, the cover 13 of the housing 10 is opened to incorporate the cartridge 2 in the heating block 40, and then the cover 13 is closed. The analyzing apparatus automatically performs sample analysis when the controller 7 recognizes a signal for starting analysis. The signal for starting analysis is generated when the user operates the switches 11a of the housing 10, or when it is recognized at the analyzing apparatus 1 that the cartridge 2 is incorporated in the heating block 40 and that the cover 13 is closed.

When the signal for starting analysis is recognized at the controller 7, the temperature of the reagents contained in the cartridge 2 is raised by the heater 4 to the target temperature (reaction temperature), and then reaction liquid is prepared.

Raising the temperature of the reagents is performed under the control of the calculator 6 in a manner such that the temperature of the heating block 40 of the heater 4 and the heating time are regulated based on the temperature (container temperature) of the cartridge 2 (seal 21) measured by the first temperature measuring member 31 and the ambient temperature about the cartridge 2 measured by the second temperature measuring member 32. The specific control procedure is described below.

Figure 5:
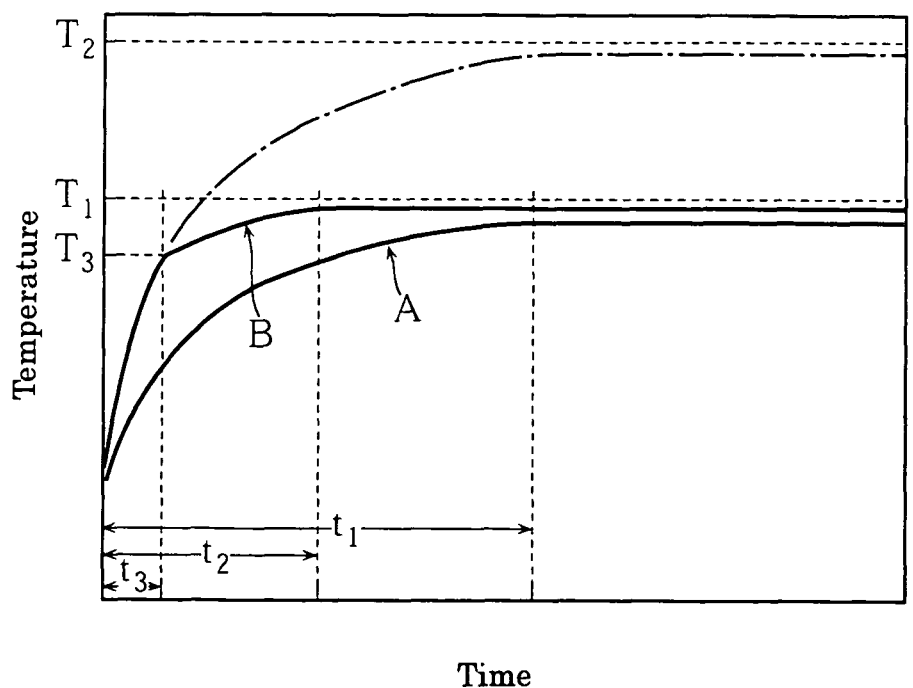
FIG. 5 is a graph illustrating examples of temperature rise curve representing the temperature of heated reagent.

First, to perform the temperature control of the heating block 40, a pre-examination is conducted for finding a correlation between the reagent-seal temperature difference occurring when a predetermined, specified period of time has lapsed from the beginning of the heating and the ambient temperature occurring when the specified time has passed. The correlation is stored in the calculator 6. The specified time may be in a range of 10 seconds to 2 minutes, and preferably in a range of 30 seconds to 1 minute. Referring to FIG. 5, a temperature rise curve A illustrates a situation where the reagents are heated up to the target temperature $T_1$. With this curve, the specified time corresponds to an initial temperature rising stage in which the temperature rising speed is relatively high. In the calculator 6, the seal temperature and the ambient temperature are evaluated based on the pre-examined correlation mentioned above, to determine the difference between the temperature of the reagents and the temperature of the seal. Then, in light of this temperature difference, the amount of heat energy to be supplied to the cartridge 2 is determined. Specifically, the temperature of the reagents is estimated by compensating the measurement of the first temperature measuring member 31 in light of the above-mentioned temperature difference, and then, based on the estimated temperature of the reagents, the amount of heat energy to be supplied is determined. Of course, the amount of heat energy to be supplied to the cartridge 2 may be determined without estimating the temperature of the reagents. The heat energy may be supplied to the cartridge 2 by either of the following two heating methods.

In a first heating method, calculation is performed to obtain a temperature rising time $t_1$ necessary for raising the temperature of the reagents up to a target temperature by supplying the maximum heat energy that the heat source is capable of generating to the heating block 40. Then, the heating block 40 is heated for the temperature rising time $t_1$ with the maximum heat energy. In this case, the temperature rise curve of the reagents looks like the curve A shown in FIG. 5. In this heating method, the temperature rising time $t_1$ is calculated based on the temperature of the reagents estimated by the calculator 6, and after the temperature rising time $t_1$ passes, the reaction liquid is prepared. The temperature rising time $t_1$ necessary for raising the temperature of the reagents may be calculated under a condition in which the temperature of the heating block 40 is raised up to a predetermined temperature in advance. In this case, the target temperature of the heating block 40 is set at the reaction temperature $T_1$ or relatively higher.

In a second heating method, a temporary target temperature of the heating block 40 is set at a temperature $T_2$ higher than the reaction temperature $T_1$, and the calculator 6 estimates the temperature of the reagents repeatedly until the temperature of the reagents comes to a switching temperature $T_3$ that is set lower than the reaction temperature. Then the target temperature of the heating block 40 is changed to the reaction temperature (true target temperature) $T_1$. The temperature $T_2$ is set at a temperature of 1.1 to 1.3 times the reaction temperature $T_1$ in centigrade, while the switching temperature $T_3$ is set at a temperature of 0.8 to 0.95 times the reaction temperature $T_1$ in centigrade. The temperature rise curve of the reagents in this heating method looks like the curve B shown in FIG. 5. In this heating method, calculation is performed to obtain a temperature rising time $t_2$ starting when the temperature of the heating block 40 is changed according to the temperature of the reagents estimated by the calculator 6 and terminating when the preparation of the reaction liquid should be started. After the time $t_2$ lapses, the reaction liquid is prepared. In the second heating method, as seen from FIG. 5, the temperature of the reagents is raised at a fast temperature rising speed until the temperature comes closer to the reaction temperature (target temperature) $T_1$, and then raised at a slower temperature rising speed after the temperature of the reagents comes closer to the reaction temperature (target temperature) $T_1$. In this manner, the temperature rising time can be shortened by increasing the temperature rising speed in the early part of the temperature raising, while the temperature of the reagents can be properly raised up to the reaction temperature (target temperature) $T_1$ by reducing the temperature rising speed in the latter part of the temperature rising.

In the second heating method, the temperature of the reagents may not be necessarily estimated repeatedly by the calculator 6. Instead, calculation may be performed to obtain a switching time $t_3$ starting from the beginning of temperature raising and ending at when the temperature of the heating block 40 is changed, and to obtain the temperature rising time $t_2$, based on the temperature of the reagents estimated by the calculator 6, thereby controlling the temperature of the heating block 40.

Preparation of reaction liquid is performed using a non-illustrated pipette provided in the housing 10. Specifically, the pipette is moved and the pipette tip 27 is attached to the pipette. Next, the pipette is moved to prepare the mixture liquid for reaction in the preparation well 24 of the cartridge 2, and then the mixture liquid and the sample in the sample well are supplied to the reaction wells 25*a*-25*c*.

After the preparation of reaction liquid completes, the controller 7 starts to measure the elapsed time. When the controller 7 recognizes that the elapsed time reaches a desired reaction time, the controller 7 controls the light source 50 to emit light to the reaction wells 25*a*-25*c*. Then, the light receiving portion 51 receives the light transmitting through the reaction wells 25*a*-25*c*, and outputs an electrical signal corresponding to the amount of the received light. The calculator 6 calculates the light transmission at the reaction wells 25*a*-25*c* based on the electrical signal from the light receiving portion 51, and then based on the light transmission, performs sample analysis, such as calculating concentration of a specific component in the sample.

According to the analyzing apparatus 1, by measuring the ambient temperature of the cartridge 2, the temperature of the reagents hermetically contained in the cartridge 2 can be estimated properly and indirectly. Therefore, the temperature of the reagents in the cartridge 2 can be raised up to a target temperature, while the reagents are kept sealed. In this way, the reagents can be prevented from evaporation until the reaction with the sample, and the reaction temperature at each analysis can be uniform. As a result, accuracy of analysis can be improved in the sample analysis that is performed after the reagents react with the sample at the target temperature.

The present invention is not limited to the above-described embodiment, but may be variously changed. For example, the heating block 40 made of e.g. metal may be replaced with a heat medium using air, water, or oil, for heating the cartridge 2 of the analyzing apparatus 1. Further, the cartridge 2 may be designed variously, and in place of the cartridge containing the plurality of reagents individually, a plurality of containers each containing one reagent may be used.

Further, in the analyzing apparatus 1, the temperature of the reagents may be raised up to the target temperature without measuring the temperature of the cartridge 2 (seal 21), but by measuring only the ambient temperature. The method in which the temperature of the cartridge 2 as well as the ambient temperature are measured is efficient when the temperature of the reagents is unknown. Differently, when the temperature of the reagents can be supposed, such as when the reagents are stored at room temperature or stored in a refrigerator and used right after being taken out thereof, the amount of heat energy to be supplied to the cartridge 2 can be determined based on the ambient temperature without measuring the temperature of the cartridge 2. In this case, heat energy is supplied to the cartridge 2 by a heating method similar to the first and the second heating methods of the analyzing apparatus 1.

Specifically, in utilizing the first heating method, the temperature rising time $t_1$ is calculated based on the correlation of the temperature difference between the reagents and the seal with the ambient temperature, both measured within the initial stage (selected from a range of 10 seconds to 2 minutes for example, or preferably from a range of 30 seconds to 1 minute after the beginning of temperature raising) where the temperature rising speed is relatively fast as seen in the temperature rise curve A representing the temperature of the reagents rising to the target temperature $T_1$, as shown in FIG. 5. Here, when the temperature difference between the reagents and the seal depends on the ambient temperature, the difference may be estimated based on the ambient temperature measured immediately before the temperature rising, and this estimated temperature difference may be used to determine the temperature rising time $t_1$.

In utilizing the second method, the temperature rising time $t_3$ necessary for raising the temperature of the reagents up to the switching temperature $T_3$ shown in FIG. 5, and the time $t_2$ necessary for raising the temperature of the reagents up to the target temperature $T_1$ from the switching temperature $T_3$, are calculated based on the correlation of the difference between the temperatures of the reagents and the seal with the ambient temperature, both measured within the initial stage (selected from a range of 10 seconds to 2 minutes for example, or preferably from a range of 30 seconds to 1 minute after the beginning of temperature raising) where the temperature rising speed is relatively fast as seen in the temperature rise curve A representing the temperature of the reagents rising to a target temperature $T_1$, as shown in FIG. 5. Here, when the temperature difference between the reagents and the seal depends on the ambient temperature, the difference may be estimated based on the ambient temperature, and this estimated temperature difference may be used to determine the time $t_3$ necessary for raising the temperature of the reagents up to the switching temperature $T_3$ and the time $t_2$ necessary for raising the temperature of the reagents up to the target temperature $T_1$.

Even the temperature raising of the reagents is based only on the ambient temperature, if the temperature of the reagents before the temperature raising can be easily estimated, the temperature of the reagents can be properly raised up to a target temperature (reaction temperature), in consideration of the ambient temperature. This method prevents variation in the analysis result due to the influence of the ambient temperature.

In temperature raising of the reagents based only on the ambient temperature, the user of the analyzing apparatus may input the status of the cartridge of the reagents (e.g. after being stored at room temperature or stored in a refrigerator and taken out thereof), so that the amount of heat energy to be supplied to the cartridge can be determined based on the data inputted by the user, in consideration of the ambient temperature. When the status (temperature) of the cartridge is kept constant, the temperature measuring member for measuring the temperature of the cartridge may be omitted from the analyzing apparatus. In this case, the structure of the analyzing apparatus as well as the calculation at the calculator can be simplified.

In the above-described second heating method for supplying energy, the heating time from the beginning to the end of supplying heat energy to the cartridge 2 is divided into two periods, however, the heating time may be divided into three periods to raise the temperature of the reagents in the cartridge 2.

The present invention may also be utilized to raise temperature of an object accommodated in a sealed container of an apparatus other than the analyzing apparatus.

EXAMPLE 1

The present example means that the reagents in the cartridge can be properly raised up to a target temperature by the above-described methods.

Figure 6:
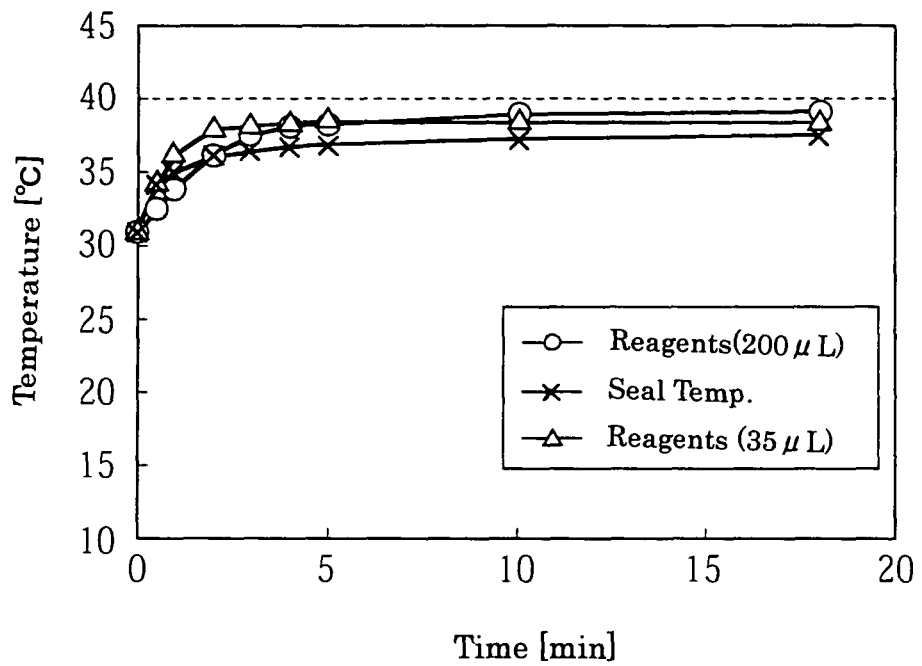
FIG. 6 is a graph illustrating the change with time of the temperatures of the reagents and of a seal of the cartridge attached to a heating block, under a condition where the ambient temperature is higher than the room temperature.
Figure 7:
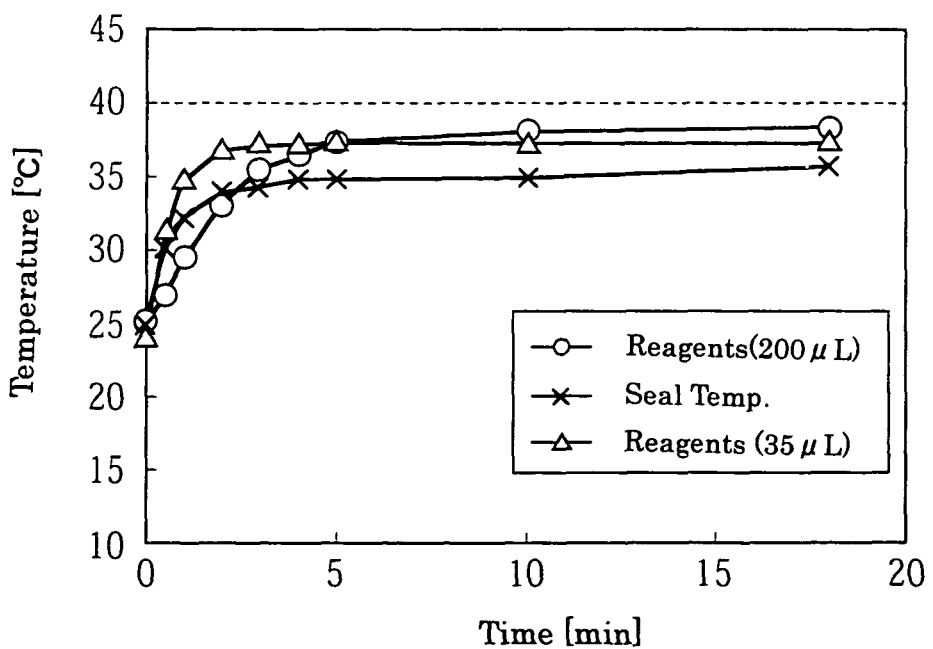
FIG. 7 is a graph illustrating the change with time of the temperatures of the reagents and the seal of the cartridge attached to the heating block, under a condition where the ambient temperature is equal to the room temperature.
Figure 8:
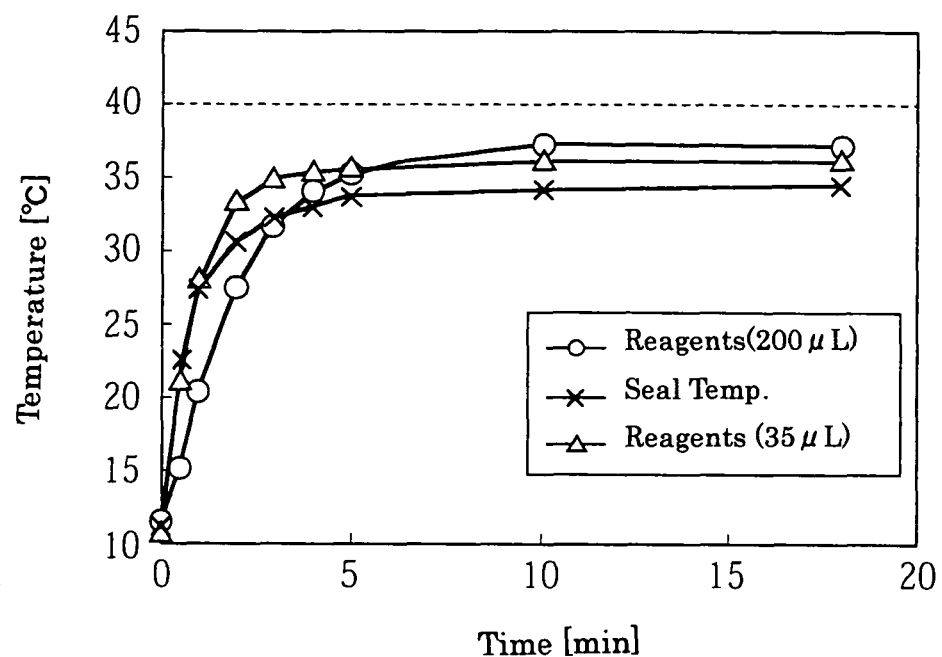
FIG. 8 is a graph illustrating the change with time of the temperatures of the reagents and the seal of the cartridge attached to the heating block, under a condition where the ambient temperature is lower than the room temperature.

In the present example, the cartridge (i-Pack CRP: manufactured by ARKRAY Inc.) was attached to the heating block, and change with time of the temperatures of the reagents and the seal of the cartridge was measured at different ambient temperatures. The temperature of the heating block was maintained at 40° C. (±0.3° C.) through feedback control. The temperature of the aluminum seal of the cartridge was measured by a thermocouple attached to the seal. The reagents to be measured were 35 µl of liquid latex and 200 µl of physiological saline solution containing saponin, of which the temperatures were measured by thermocouples put into the reagents. The ambient temperature was set at 28.1° C. (with 21% relative humidity), 23.6° C. (with 25% relative humidity) that is equal to the room temperature, and 11.3° C. (with 30% relative humidity). The measurement results at the ambient temperatures are respectively shown in FIGS. 6-8.

As seen from the figures, the temperature of each of the reagents was affected by the ambient temperature, and as the ambient temperature was lowered, the temperature of each reagent deviated from the temperature of the heating block. Further, in the stage before the temperature of each reagent approaches a predetermined temperature (during the first one minute after the heating, for example), correlation seemed to exist between the temperature difference of the seal and the reagents and the ambient temperature. For specific consideration on this point, the relationship of the temperature difference between the seal and the reagents with the ambient temperature was examined at 0.5 and 1.0 minute after the beginning of heating, based on the measurement results shown in FIGS. 6-8. The result of study is shown in FIG. 9.

Figure 9:
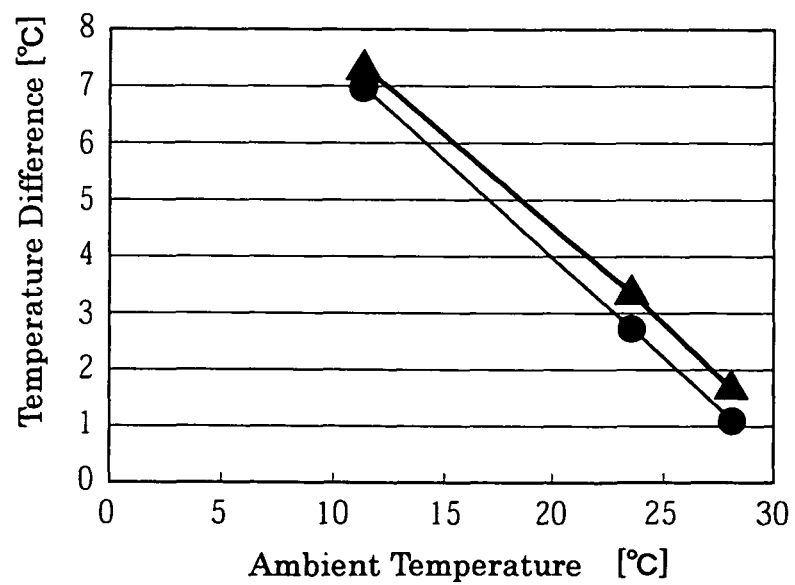
FIG. 9 is a graph illustrating a relationship of the temperature difference between the reagents and the seal with the ambient temperature, based on the measurement results shown in FIGS. 6-8.

As seen from FIG. 9, at 0.5 and 1.0 minute after the beginning of heating, a linear correlation existed between the temperature difference of the seal and the reagents and the ambient temperature. Thus, due to the previously examined correlation of the temperature difference between the seal and the reagents with the ambient temperature in the stage before the temperature of each reagent approaches a predetermined temperature, the temperature of the reagents can be properly estimated by measuring the temperature of the seal and the ambient temperature and by assigning the measurement results to the correlation. As a result, the temperature of the reagents can be raised up to a target temperature (reaction temperature) without being affected by the ambient temperature, and thus the reaction temperatures are uniform, thereby improving accuracy of analysis.

The invention claimed is:

1. A method of raising a temperature of an object contained hermetically in a container to a predetermined temperature, the method comprising:
   a first step of measuring a temperature of the container and an ambient temperature around the container;
   a second step of estimating the temperature of the contained object based on the container temperature and the ambient temperature, the second step including
      pre-examining a correlation between a temperature difference of contained object and temperature of a container and the ambient temperature, measured during a predetermined period of time starting from the beginning of raising the temperature, the predetermined period of time being within a range of 10 seconds to 2 minutes, and calculating, the estimated temperature of the contained object based on the pre-examined correlation,
   a third step of determining an amount of heat energy necessary for raising the temperature of the contained object up to the predetermined temperature, the determination being based on the container temperature and the ambient temperature;
   a fourth step of supplying heat energy to the container, based on a result of the second step.

2. The method of raising a temperature of a contained object according to claim 1, wherein the container comprises a receptacle having an opening and a seal for sealing the opening,
   wherein the measurement of the container temperature in the first step is performed at the seal.

3. The method of raising a temperature of a contained object according to claim 1,
   wherein in the third step, the estimated temperature is checked to be higher or lower than an additional predetermined temperature set lower than said predetermined temperature, and wherein the amount of heat energy to be supplied to the container is determined based on the check result.

4. The method of raising a temperature of a contained object according to claim 3, wherein in the third step, the amount of heat energy to be supplied to the container is determined so that the amount of heat energy to be supplied to the container per unit time is smaller when the estimated temperature is higher than the additional predetermined temperature, than when the estimated temperature is lower than the additional predetermined temperature.

5. The method of raising a temperature of a contained object according to claim 1, wherein the predetermined time is set for an initial stage of raising the temperature of the contained object up to the predetermined temperature where a temperature rising rate of the contained object and the container per unit time is relatively large.

6. The method of raising a temperature of a contained object according to claim 1, wherein in the fourth step, the container is brought into contact with a heat medium, and control of the amount of heat energy to be supplied to the container is performed by controlling the temperature of the heat medium.

7. The method of raising a temperature of a contained object according to claim 6, wherein the heat medium is a heating block.

8. A method of raising a temperature of a contained, object sealed in a container, up to a predetermined temperature, by supplying heat energy to the container brought into contact with a heating block, the method comprising:
   a first step of measuring, ambient temperature around the container immediately before raising the temperature;
   a second step of determining an amount of heat energy necessary for raising the temperature of the contained object up to the predetermined temperature, based on the ambient temperature, the second step including
      pre-examining a correlation between the ambient temperature and a difference between the temperatures of the contained object and the container, measured during a predetermined period of time, which is within a range of 10 seconds to 2 minutes, and
      calculating the amount of heat energy based on the pre-examined correlation; and
   a third step of supplying heat energy to the container via the heating block, based on a result of the second step.

9. The method of raising a temperature of a contained object according to claim 8, wherein in the second step, the amount of heat energy to be supplied to the container is controlled by setting a temperature of the heating block and setting a time that the set temperature of the heating block is to be maintained.

10. The method of raising a temperature of a contained object according to claim 8, wherein in the second step, the supplied time of the heat energy is divided into a first period from a beginning of the supply of the heat energy until a predetermined time passes, and a second period from an end of the predetermined time until the supply of the heat energy ends,
   wherein the amount of heat energy to be supplied to the container is regulated so that the amount of heat energy to be supplied per unit time is smaller in the second period than in the first period.

11. The method of raising a temperature of a contained object according to claim 8, wherein the predetermined time is set within an initial stage of raising the temperature of the contained object up to the predetermined temperature where the temperature rising amount of the contained object and the container per unit time is relatively large.

* * * * *